United States Patent
Liebowitz

(10) Patent No.: US 6,645,173 B1
(45) Date of Patent: Nov. 11, 2003

(54) DRIPLESS EARDROP APPLICATOR

(76) Inventor: Barbara Liebowitz, P.O. Box 212, Belford, NJ (US) 07718

( * ) Notice: Subject to any disclaimer, the term of this patent is extended or adjusted under 35 U.S.C. 154(b) by 0 days.

(21) Appl. No.: 10/109,923

(22) Filed: Mar. 29, 2002

(51) Int. Cl.[7] .............................................. A61M 11/00
(52) U.S. Cl. ......................... 604/94; 604/27; 604/514; 604/80
(58) Field of Search ................. 604/289, 294–302, 604/2, 27, 48, 514, 80, 93, 94; 81/130, 135; 2/422, 413, 209; 128/204.11; 222/175; 224/181

(56) References Cited

U.S. PATENT DOCUMENTS

| | | | | |
|---|---|---|---|---|
| 989,839 A | * | 4/1911 | Fowler | 604/276 |
| 1,500,927 A | * | 7/1924 | Davies et al. | 604/346 |
| 4,036,235 A | * | 7/1977 | Hathaway | 604/346 |
| 4,201,212 A | * | 5/1980 | Bradley | 604/346 |
| 4,739,905 A | * | 4/1988 | Nelson | 222/145.4 |
| 5,364,343 A | * | 11/1994 | Apolet et al. | 604/43 |
| 5,395,357 A | * | 3/1995 | Weigel | 604/346 |
| 5,993,428 A | * | 11/1999 | Hardge | 604/294 |
| 6,210,258 B1 | * | 4/2001 | Malkin et al. | 451/74 |

* cited by examiner

*Primary Examiner*—Weilun Lo
*Assistant Examiner*—Linh Truong
(74) *Attorney, Agent, or Firm*—Michael I Kroll

(57) ABSTRACT

The present invention 10 discloses a medication dispensing device which can be attached to the head of an individual 12 via a head band 30 having a medicinal depository reservoir 16 located at the top of the head band 30 wherein a measured amount of liquid medication 22 would be inserted therein and the device would hold the medication 22 until released whereby the medication would then travel down a length of conduit 18 until being dispensed into the ear canal 36 through an earpiece 34.

15 Claims, 9 Drawing Sheets

DRIPLESS EARDROP APPLICATOR

BACKGROUND OF THE INVENTION

1. Field of the Invention

The present invention relates generally to medication dispensing devices and, more specifically, to a device which can be attached to the head of an individual, much as a head band, having a medicinal depository container located at the top of the head band wherein a measured amount of liquid medication would be inserted wherein the device would hold the medication until released whereby the medication would travel down a length of conduit until being dispensed into the ear canal through an earpiece.

2. Description of the Prior Art

There are other ear piece devices designed to hold or be inserted into the ear. Typical of these is U.S. Pat. No. 4,006,796 issued to Coehorst on Feb. 8, 1977.

Another patent was issued to Lundin on Jun. 23, 1987 as U.S. Pat. No. 4,674,134. Yet another U.S. Pat. No. 4,971,072 was issued to Randall on Nov. 20, 1990.

U.S. Pat. No. 4.006,796

Inventor: Robert Francois Coehorst

Issued: Feb. 8, 1977

An earpiece which takes the form of a pouch made of a plastic foil which surrounds a less pliant plastic tube in an airtight manner and is filled with a sluggishly moving jelly-like paste. A not readily movable compression ring provided with a funnel shaped portion which is clear of the tube ensures that the pouch perfectly engages with the inner wall of the auditory canal.

U.S. Pat. No. 4,674,134

Inventor: Tord R. Lundin

Issued: Jun. 23, 1987

An earmuff (10) has a sealing ring (20) with an outer liquid layer (38) and a foamed plastic layer (36) therein under. The liquid layer is arranged as a separate, annular, sheath-equipped liquid ring (38) the sheath (40) of which can move freely relative the sheath (30,32) of the sealing ring (20).

U.S. Pat. No. 4,971,072

Inventor: Carol C. Randall

Issued: Nov. 20, 1990

A brace to hold the ears in a position folded forward and down having a pair of like spring clips attached with rivets to either end of an elastic strap.

While these earpiece devices may be suitable for the purposes for which they were designed, they would not be as suitable for the purposes of the present invention, as hereinafter described.

SUMMARY OF THE PRESENT INVENTION

The present invention discloses a medication dispensing device which can be attached to the head of an individual via a head band having a medicinal depository reservoir located at the top of the head band wherein a measured amount of liquid medication would be inserted into the reservoir and the device would hold the medication until released whereby the medication would then travel down a length of conduit until being dispensed into the ear canal of the user through an earpiece.

A primary object of the present invention is to provide a headband like device for administering amounts of liquid medication into the ear canal without spillage.

Another object of the present invention is to provide a headband like device having a medicinal depository container attached thereon for administering amounts of liquid medication into the ear canal without spillage.

Yet another object of the present invention is to provide a head band like device having a medicinal depository container attached thereon having an amount of conduit connected to an earpiece for administering amounts of liquid medication into the ear canal without spillage.

Additional objects of the present invention will appear as the description proceeds.

The present invention overcomes the shortcomings of the prior art by providing a device which can be attached to the head of an individual having a medicinal depository container located at the top of the head band wherein a measured amount of liquid medication would be inserted wherein said device would hold said medication until released whereby said medication would travel down a length of conduit until being dispensed into the ear canal through an earpiece.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views in which.

LIST OF REFERENCE NUMERALS

Figure 1:
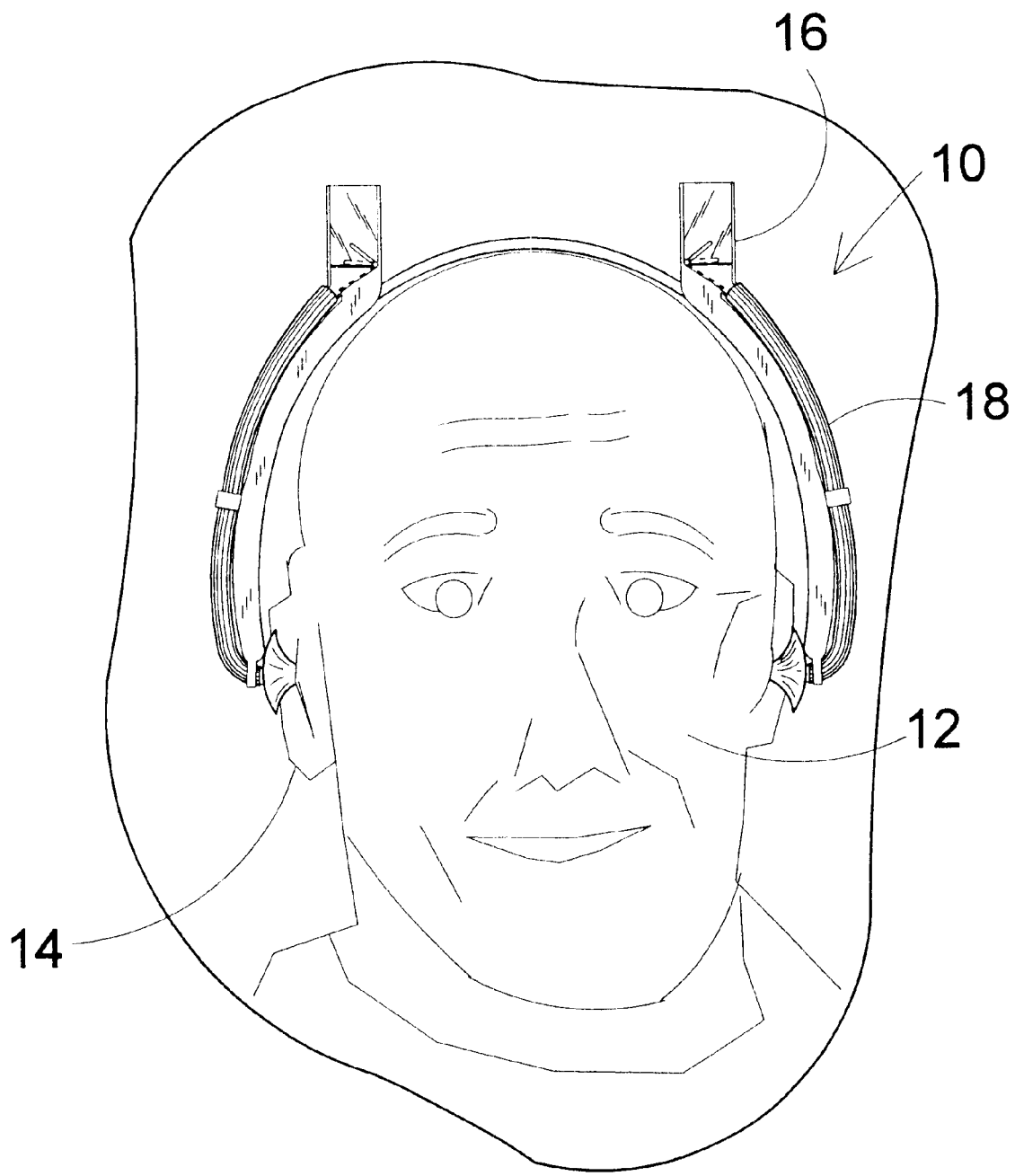
FIG. 1 is a perspective view of the present invention in use.

With regard to reference numerals used, the following numbering is used throughout the drawings.
10 present invention
12 user
14 ear
16 reservoir
17 outlet
18 conduit
20 medication drop
22 medication
24 medicine dropper
26 release lever
28 retaining plate
30 head band
32 hand of user
34 earpiece
36 ear canal
38 adjustment means
40 attachment member
42 clamp
44 duct

DETAILED DESCRIPTION OF THE PREFERRED EMBODIMENTS

The following discussion describes in detail one embodiment of the invention and several variations of that embodiment. This discussion should not be construed, however, as limiting the invention to those particular embodiments, practitioners skilled in the art will recognize numerous other embodiments as well. For definition of the complete scope of the invention, the reader is directed to appended claims.

Turning to FIG. 1, shown therein is a perspective view of the present invention 10 in use. Shown is an individual 12 using the present invention whereby a measured amount of medication is deposited into a reservoir for dispensing into the ear 14 or ears by means of conduit 16.

Figure 2:
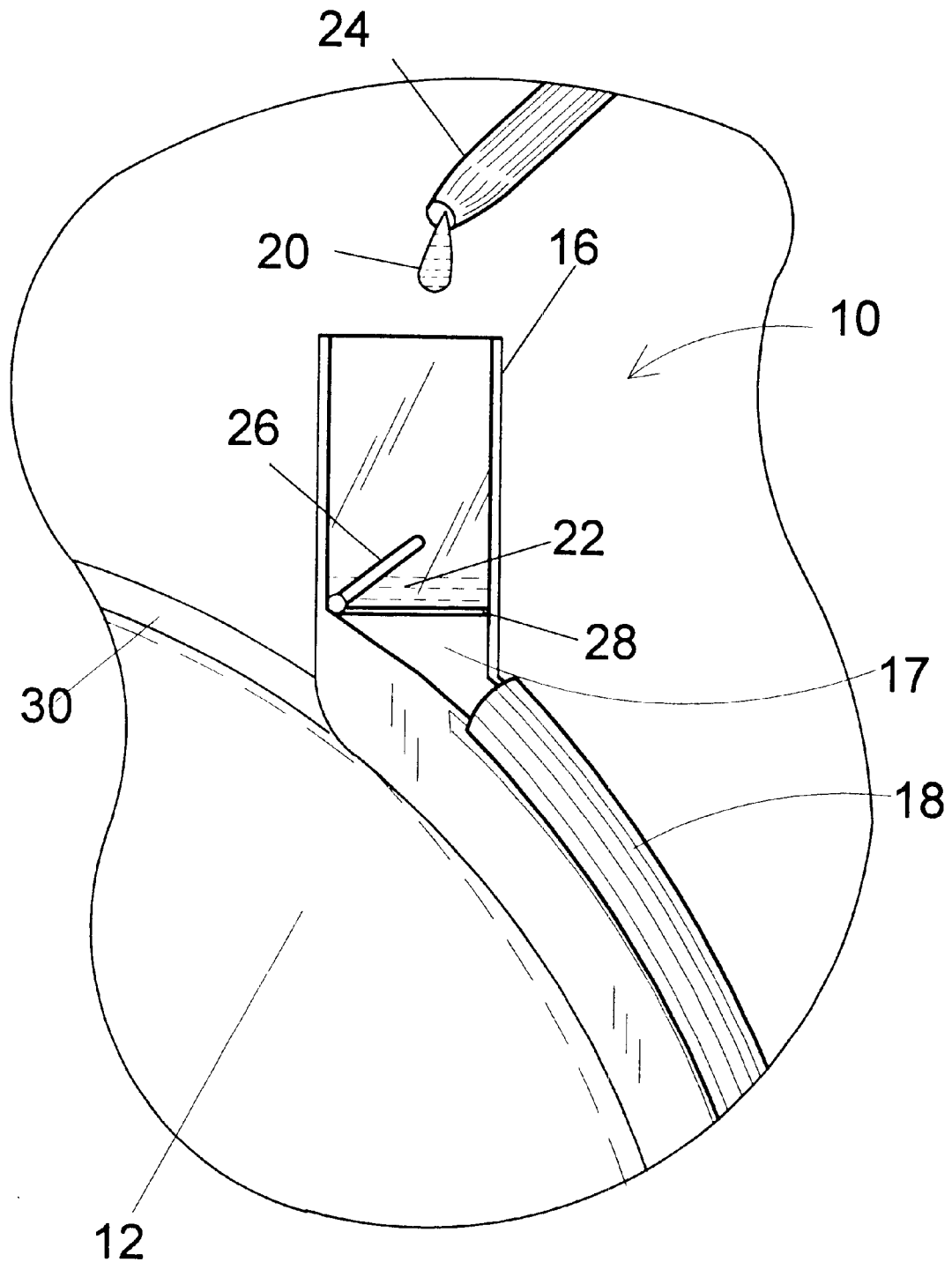
FIG. 2 is an enlarged view of the reservoir of the present invention.

Turning to FIG. 2, shown therein is an enlarged view of the reservoir 16 of the present invention 10. Shown is a reservoir container 16 having an outlet 17 being open at the top allowing insertion of a small amount or drop 20 of medication, wherein the container 16 has means for releasing the medicinal contents 22 of the container. Also shown is a medicine dropper 24 dispensing the medicine into the reservoir 16 along with a release lever 26 and retaining plate 28. Also shown are the conduit 18, head of user 12 and headband 30.

Figure 3:
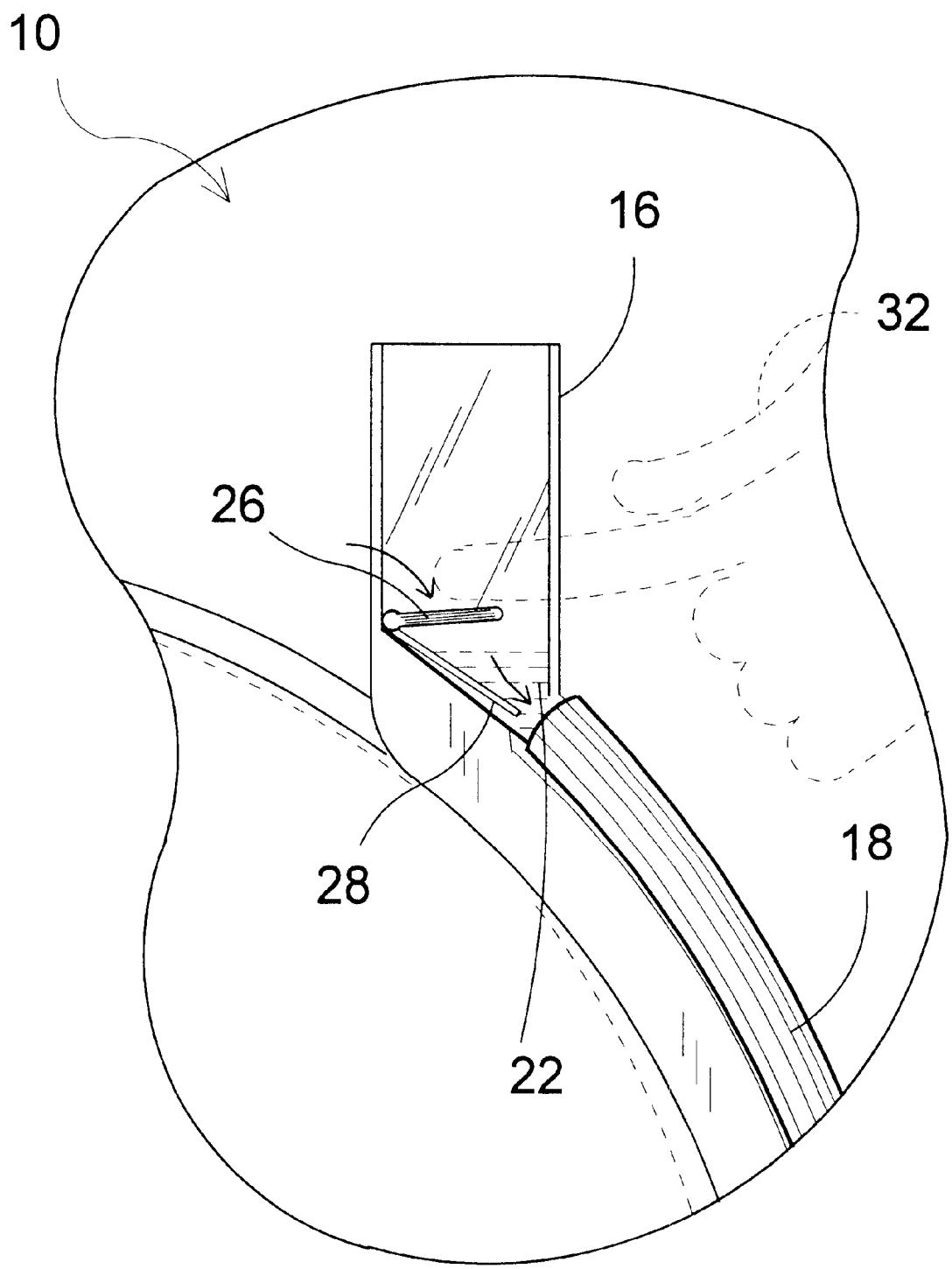
FIG. 3 is an enlarged view of the reservoir of the present invention.

Turning to FIG. 3, shown therein is an enlarged view of the reservoir 16 of the present invention 10. Shown is a container 16 having means for releasing the contents of the container and a hand 32 shown in outline depressing a lever 26 whereby the liquid medication 22 is released into a conduit 18 leading into an earpiece having an aperture leading into the ear canal. Retaining plate 28 is also shown.

Figure 4:
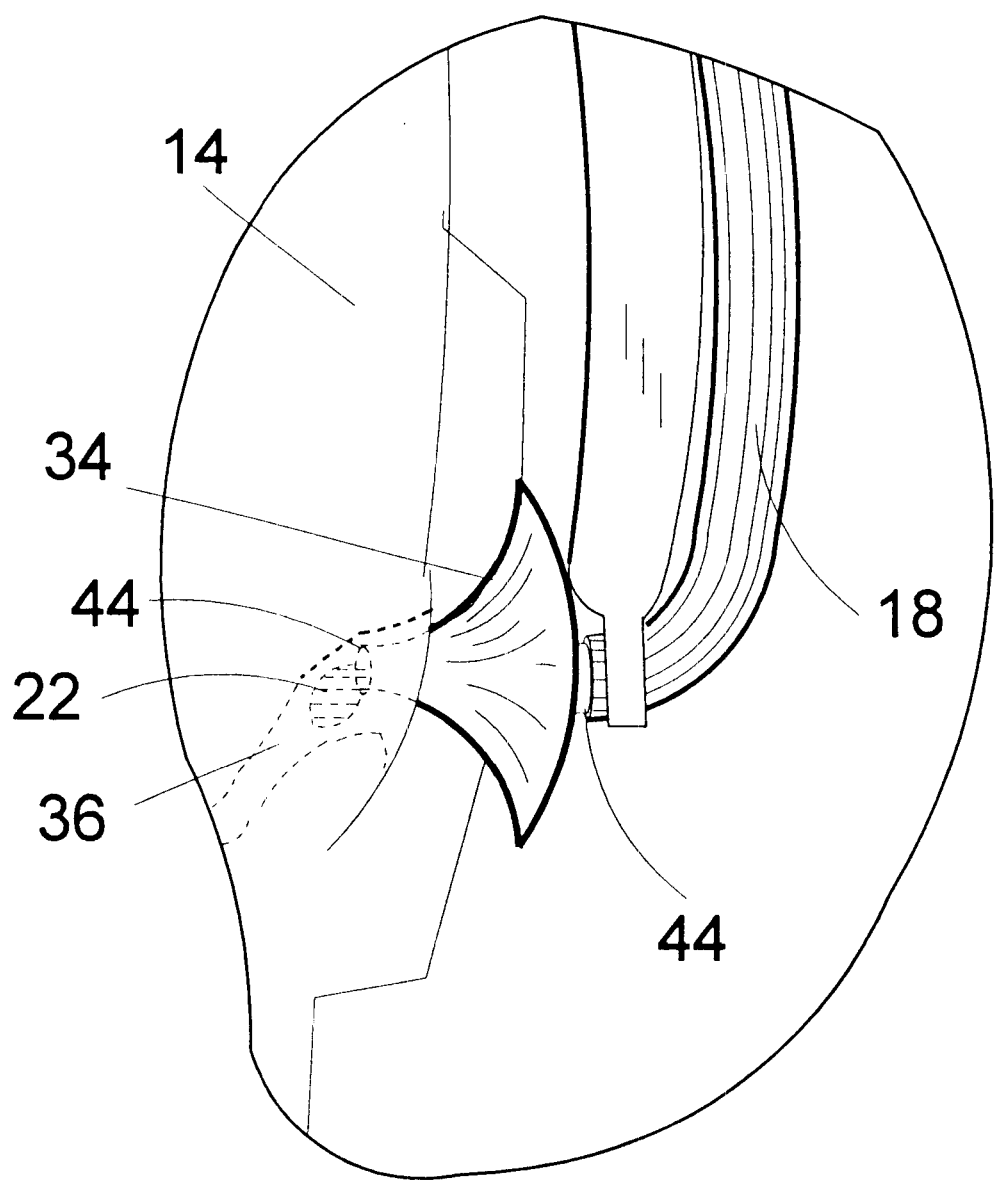
FIG. 4 is an enlarged view of an ear having one of a pair of earpieces inserted therein.

Turning to FIG. 4, shown therein is an enlarged view of an ear 14 having one of a pair of earpieces 34 being shaped somewhat like an earplug inserted therein having means for sealing the earpiece 34 to the ear 14 wherein the medication will be inserted into the ear canal 36. The earpiece 34 has a duct 44 therein having an inlet and an outlet through which medication 22 can flow. The earpiece 34 is somewhat frusto-conical shaped.

Figure 5:
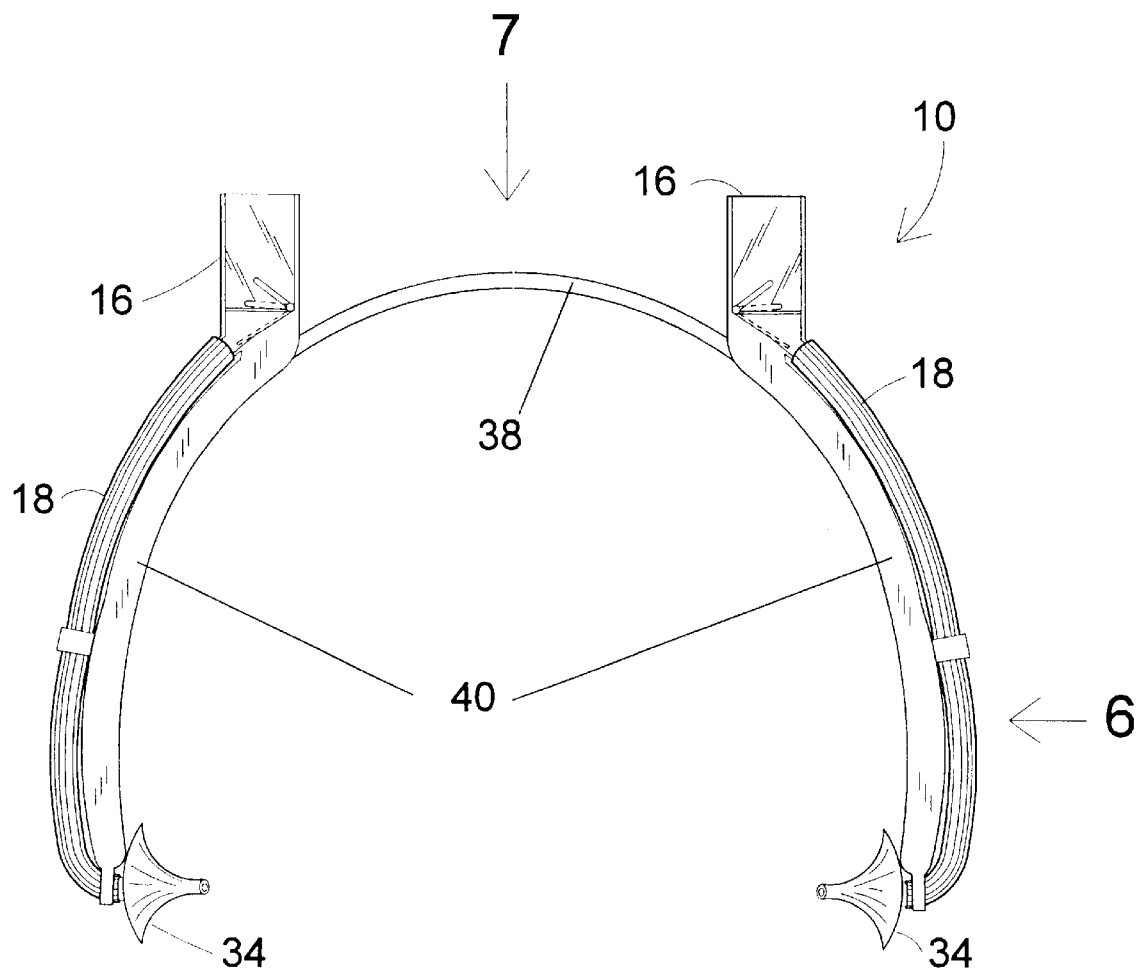
FIG. 5 is a top view of the present invention.

Turning to FIG. 5, shown therein is a front view of the present invention 10 showing an adjusting means 38 with two opposing ends, each end engagably slides within a channel inside an attachment member 40 for changing the size of the device accordingly to head size for the needs of each user, each attachment member having secured thereon a medicinal depository 16 having means for opening and closing the depository which allows the medication by means of conduit 18 to travel to an earpiece 34 having means to seal the earpiece to the ear wherein the medication will be deposited into the ear canal without spillage.

Figure 6:
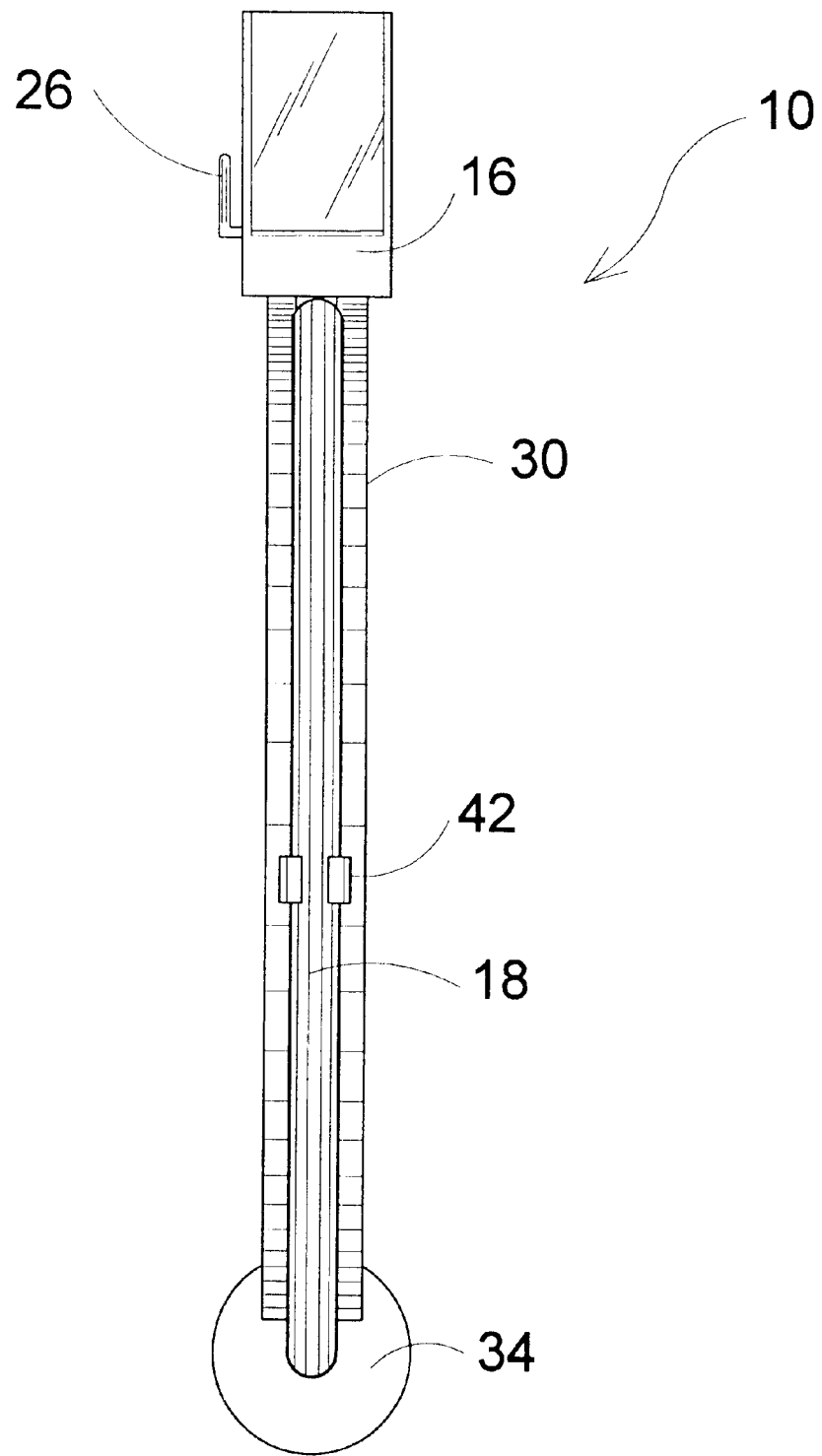
FIG. 6 is a side elevation view of the present invention.

Turning to FIG. 6, shown therein is a side elevation view of the present invention 10. Shown is the medicinal depository reservoir 16 having a release lever 26 being attached to a head band 30 having a length of conduit 18 between the medicinal depository 16 and an earpiece 34 and wherein the head band 30 has attachment or clamp means 42 for the conduit.

Figure 7:
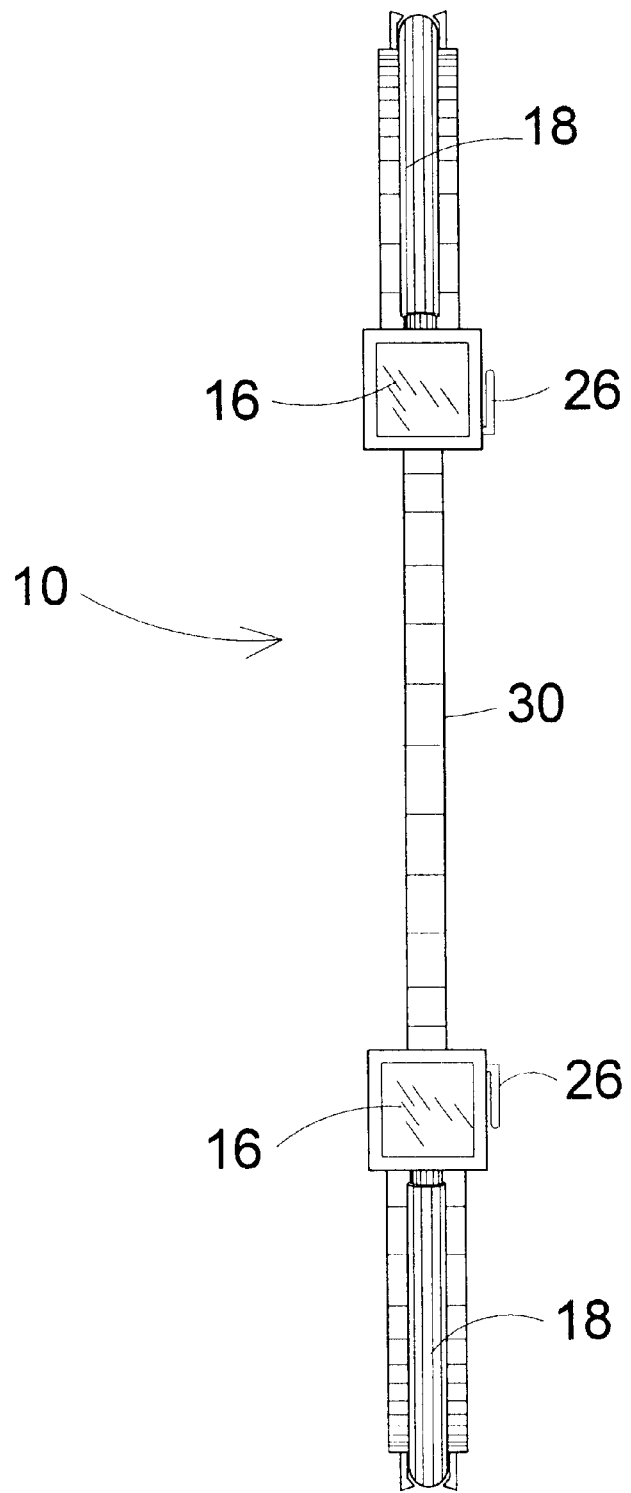
FIG. 7 is a top plan view of the present invention.

Turning to FIG. 7, shown therein is a top plan view of the present invention 10. Shown is the medicinal depository 16 having a release lever 26 being attached to a head band 30 having a length of conduit 18 attached to the medicinal depository 16 providing means for delivering liquid medicine to an ear.

Figure 8:
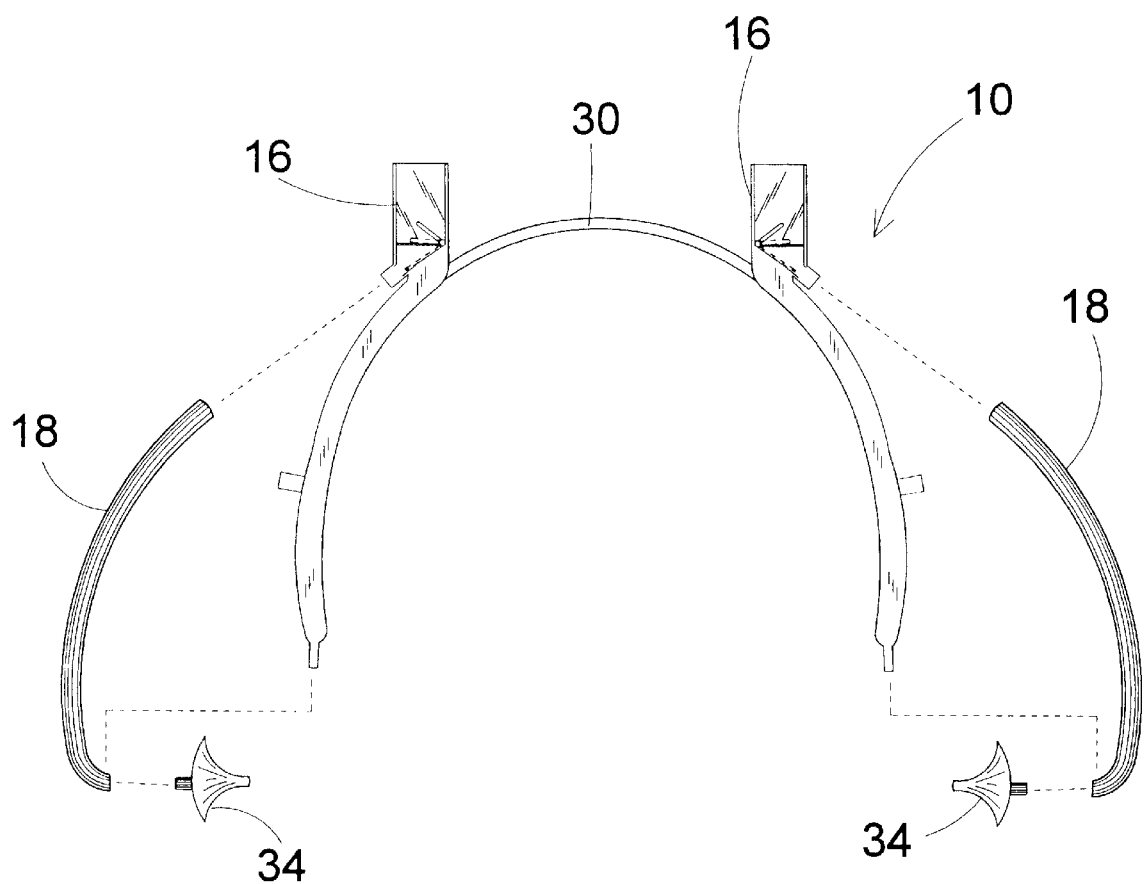
FIG. 8 is an exploded front view of the present invention.

Turning to FIG. 8, shown therein is a front view of the present invention 10. Shown is a device being comprised of a head band 30 having means for adjusting the size of the head band having attached thereon a medicinal depository container 16 having means for opening and closing the depository and a length of conduit 18 which channels the medication to an earpiece 34 having means to seal the earpiece to an ear.

Figure 9:
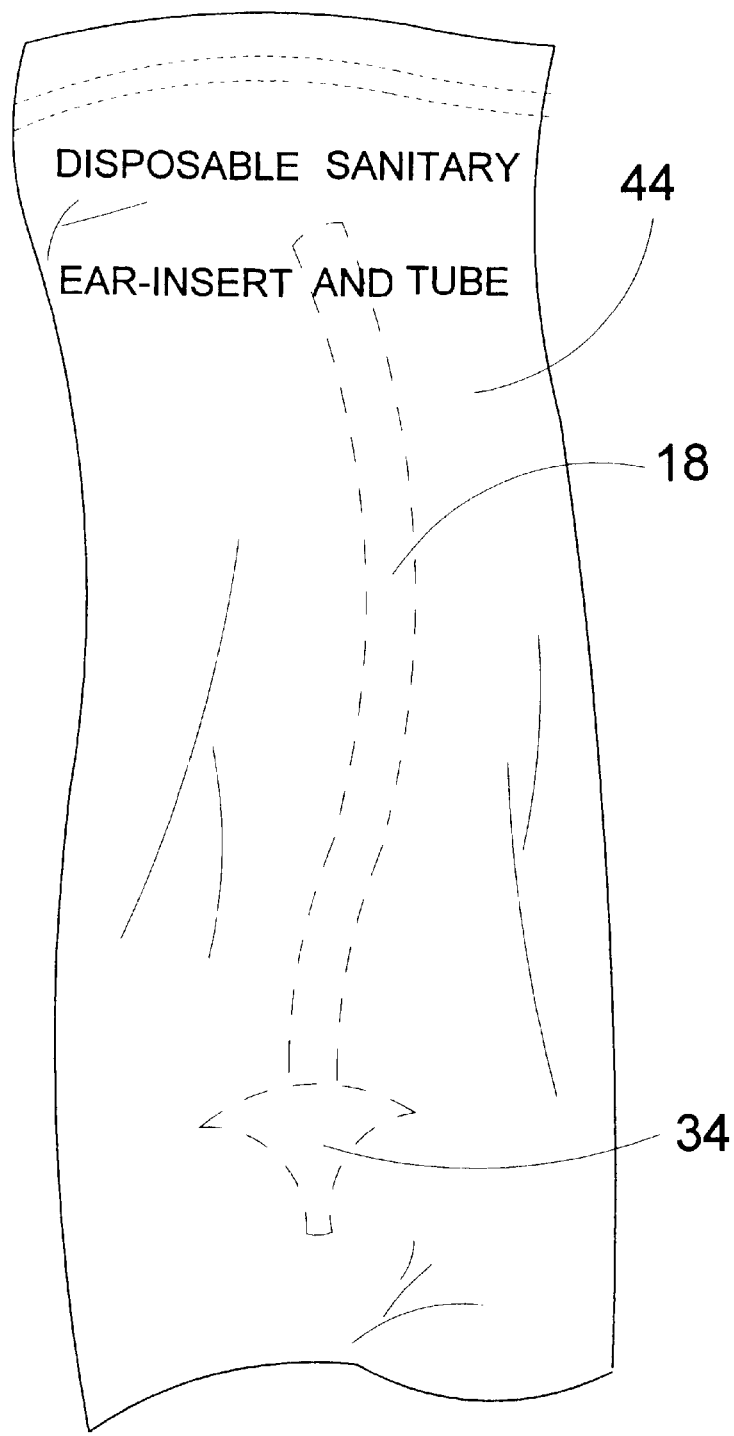
FIG. 9 is a front elevation of the earpiece and conduit of the present invention packaged in a hermetically sealed bag.

Turning to FIG. 9, shown therein is a front elevation of the earpiece 34 and conduit 18 of the present invention being packaged in a hermetically sealed, disposable, sanitary bag 44 wherein the earpiece 34 and conduit 18 can be disposed of and replaced as needed.

What is claimed to be new and desired to be protected by Letters Patent is set forth in the appended claims.

I claim:

1. An apparatus capable of dispensing a measured amount of liquid medication directly into the ears of a user, comprising:

a) a pair of reservoirs for containing liquid medication adapted to be disposed on the head of a user, said reservoirs each having an opening for receiving a measured amount of medication to be delivered to said ears;

b) means adapted for securely attaching said reservoirs to the head of a user;

c) a pair of earpieces capable of being disposed in the ears of a user for allowing medication to be dispensed directly into ear canals of the user, each of said earpieces having generally the shape of an ear plug to fit the ear of a user and a duct therein for transmitting flow of medication;

d) a fluid connection of said reservoirs to said pair of earpieces; and, e) means for releasing the medication from said reservoirs through said fluid connection allowing delivery of the measured amount of medication to the ear canals of the user.

2. The apparatus of claim 1, wherein said reservoirs are rectangular shaped, said reservoirs being open on the top for receiving the liquid medication.

3. The apparatus of claim 2, wherein said means for attaching said reservoirs further comprises an arcuate head band, said head band adapted to be supported on the head of the user and adjustable to fit the head of the user.

4. The apparatus of claim 3, further comprising a pair of attachment members, said attachment members having a first end and a second end, said attachment members being arcuate shaped, said attachment members having a channel therein, said first end of said channel for receiving one end of said head band, said head band being slidable within said attachment member so that the size of said head band is adjustable about the head of the user.

5. The apparatus of claim 4, wherein said reservoirs are disposed on said first end of said attachment members.

6. The apparatus of claim 1, wherein said earpiece has a frustoconical shape for easy insertion into the ear of the user.

7. The apparatus of claim 6, wherein said fluid connection further comprises a pair of conduits disposed on said attachment members, said conduits connecting said reservoirs to said earpieces.

8. The apparatus of claim 7, further comprising at least one clamp disposed on said attachment member, said clamp for removably, fixedly receiving said conduit so that said conduit is attached to said attachment member.

9. The apparatus of claim 8, wherein said conduit further comprises a flexible tube.

10. The apparatus of claim 9, wherein said means for releasing the medication from said reservoirs further comprises an outlet disposed in the base of said reservoir, said outlet having a movable retaining plate disposed across said outlet so as to close said outlet of said reservoir.

11. The apparatus of claim 10, wherein said means for releasing the medication from said reservoir further comprises a release lever disposed external of said reservoir, said release lever being in operative connection with said retaining plate.

12. The apparatus of claim 11, wherein said retaining plate is movable in response to movement of said release lever so that said outlet of said reservoir is thereby opened by movement of said release lever by the user.

13. The apparatus of claim 12, further comprising a disposable sanitary bag for insertion of said earpiece and said conduit therein for disposal of said earpiece and said conduit.

14. The apparatus of claim 6, wherein said ear piece is shaped to form a seal within the ear of the user.

15. The method of delivering a measured amount of liquid medication directly into the ears of a user comprising the steps of:

a) mounting on a head of a user a reservoir having an upper opening and a bottom opening normally closed by a valve;

b) inserting an earpiece with a passage therethrough directly into an ear of the user;

c) joining the bottom opening of said reservoir to said earpiece with a fluid connection;

d) dropping into said reservoir through said upper opening a measured amount of said medication; and e) opening said valve in the bottom opening of said reservoir to allow said measured amount of medication to flow through said fluid connection and said earpiece into said ear.

* * * * *